United States Patent [19]

Furman et al.

[11] Patent Number: 5,883,059

[45] Date of Patent: Mar. 16, 1999

[54] THREE IN ONE ULTRA MILD LATHERING ANTIBACTERIAL LIQUID PERSONAL CLEANSING COMPOSITION

[75] Inventors: Christopher Allen Furman, Fairfield, Ohio; Michel Joseph Giret, Camberley, Great Britain; James Charles Dunbar, West Chester; Jon Joseph Damiano, Sharonville, both of Ohio

[73] Assignee: The Procter & Gamble Company, Cincinnati, Ohio

[21] Appl. No.: 720,692

[22] Filed: Oct. 2, 1996

Related U.S. Application Data

[63] Continuation of Ser. No. 531,487, Sep. 21, 1995, abandoned, which is a continuation of Ser. No. 370,073, Jan. 9, 1995, abandoned.

[51] Int. Cl.$^6$ .............................. C11D 1/16; C11D 1/88; C11D 3/48
[52] U.S. Cl. ..................... 510/130; 510/131; 510/137; 510/138; 510/155; 510/156; 510/159; 510/384; 510/386; 510/414; 510/433; 510/426
[58] Field of Search ................... 510/130, 131, 510/137, 155, 156, 159, 384, 386, 414, 433, 426

[56] References Cited

U.S. PATENT DOCUMENTS

| | | | |
|---|---|---|---|
| 2,396,278 | 3/1946 | Lind | 252/138 |
| 2,486,921 | 11/1949 | Byerly | 252/138 |
| 3,480,616 | 11/1969 | Osipow et al. | 260/234 |
| 3,835,057 | 9/1974 | Cheng | 252/107 |
| 3,929,678 | 12/1975 | Laughlin et al. | 252/526 |
| 4,310,433 | 1/1982 | Stiros | 252/132 |
| 4,338,211 | 7/1982 | Stiros | 252/142 |
| 4,565,647 | 1/1986 | Llenado | 252/354 |
| 4,714,563 | 12/1987 | Kajs et al. | 252/107 |
| 4,740,367 | 4/1988 | Force et al. | 424/47 |
| 4,835,148 | 5/1989 | Barford et al. | 514/179 |
| 4,842,850 | 6/1989 | Vu | 424/70 |
| 4,851,154 | 7/1989 | Grollier et al. | 252/546 |
| 5,308,526 | 5/1994 | Dias et al. | 252/125 |
| 5,312,559 | 5/1994 | Kacher et al. | 252/125 |
| 5,409,640 | 4/1995 | Giret et al. | 252/546 |
| 5,681,802 | 10/1997 | Fujiwara et al. | 510/130 |

FOREIGN PATENT DOCUMENTS

92/18100 10/1992 WIPO.

*Primary Examiner*—Paul Lieberman
*Assistant Examiner*—Charles Boyer
*Attorney, Agent, or Firm*—Darryl C. Little; Tara M. Rosnell; George W. Allen

[57] ABSTRACT

A mild antibacterial liquid personal cleanser compositions. (More specifically, a mild, lathering compositions, especially those that are useful for application to the body, face and hands.) comprising:

(a) from about 0.1 parts to about 20 parts, preferably 1 part to 15 parts, especially 3 to 12 parts by weight of anionic surfactant, (b) from about 0.1 parts to about 20 parts, preferably 1 part to 15 parts, especially 3 to 12 parts by weight of amphoteric surfactant, (c) from about 0.5 parts to about 25 parts, preferably 0.5 parts to 15 parts, especially 3 parts to about 10 parts by weight of an oily skin moisturizer, preferably an adduct prepared from vegetable oils containing non-conjugated polyunsaturated fatty acid esters which are conjugated and elaidinized and then modified via Diels-Alder addition with a member of the group consisting of acrylic acid, fumaric acid and maleic anhydride, (d) from about 0.1 parts to about 2.0 parts antibacterial agent, and (e) water, wherein the anionic surfactant and amphoteric surfactant together comprise from about 0.5 parts to about 30 parts, preferably 5 parts to 25 parts, especially 10 parts to 20 parts by weight of the composition, and where the weight ratio of anionic surfactant:amphoteric surfactant is in the range from about 1:5 to about 20:1, preferably 1:2 to about 5:1, especially 1:1 to about 2:1.

8 Claims, No Drawings

ABSTRACT # THREE IN ONE ULTRA MILD LATHERING ANTIBACTERIAL LIQUID PERSONAL CLEANSING COMPOSITION

This is a continuation of application Ser. No. 08/531,487, filed on Sep. 21, 1995, now abandoned, which is a continuation of application Ser. No. 08/370,073, filed on Jan. 9, 1995, now abandoned.

TECHNICAL FIELD

The present invention is related to mild antibacterial liquid personal cleanser compositions. More specifically, the present invention relates to mild, lathering compositions, especially those that are useful for application to the body, face and hands.

BACKGROUND OF THE INVENTION

The cleaning of skin with surface-active cleaning preparations has become a focus of great interest. Many people wash and scrub their skin with various surface active preparations several times a day. Liquid cleansers are highly preferred, especially for the body, because of convenience and non-messiness. Antibacterial personal cleansers are preferred because they kill germs. Mild personal cleansers are desired to minimize skin irritation, dryness, etc. A personal cleansing product having all three of these preferred characteristics would be very desirable.

Skin cleansers should cleanse the skin gently, causing little or no irritation, without drying the skin after frequent routine use. Certain synthetic surfactants are particularly mild. However, a major drawback of mild liquid synthetic surfactant systems when formulated for skin cleansing is poor lather performance. Compared to the highest bar soap standards (bars which are rich in coconut soap and superfatted), these prior art liquid surfactant formulations have either poor lather or poor skin mildness performance. As may be expected, the lather performance is a function of the choice of surfactant and its concentration. The conceivable number of liquid surfactant compositions formulated with or without skin feel agents are numerous. Rheological and phase properties exhibited by prototypes vary widely (i.e., thin liquids, gels, thick pastes, solutions, emulsions). The phase stability of prototypes is for the most part acceptable over short time periods, but only a small fraction of them will maintain their original properties and acceptability over an extended period of time. See, e.g., U.S. Pat. No. 4,338,211, Stiros, issued Jul. 6, 1982; U.S. Pat. No. 4,310,433, Stiros, issued Jan. 12, 1982; and U.S. Pat. No. 4,842,850, Vu, issued Jun. 27, 1989, all of said patents being incorporated herein by reference.

Optimization of lather as a single variable is a fairly straightforward process. The use of known high sudsing anionic surfactants with lather boosters yields acceptable lather volume. Unfortunately, highest sudsing anionic surfactants are, generally, also highest in skin irritation and are worst in clinical mildness. Surfactants that are among the mildest with minimal skin irritation, such as ammonium lauryl ether (12 EO) sulfate ($NH_4AE_{12}S$) are extremely poor in lather. These two facts alone make the surfactant selection and the lather boosting optimization process a delicate balancing act. See, e.g., U.S. Pat. No. 4,338,211, supra, incorporated herein by reference.

The introduction of an antibacterial into the equation results in additional problems for mildness, lather, and efficacy. It is reported in trade literature that certain mild ethoxylated nonionic surfactants, e.g., TweenR 80 (ICI Americas, Inc.) and lecithin have deactivating effects on the degerming of a preferred antibacterial, Triclosan (IrgasanR DP 300 is also referred to herein as "TCS"), Ciba-Geigy IrgasanR DP 300 Trade Bulletin, 1988.

In short, there are rather stringent requirements for skin cleansers which limit the choice of surface-active agents and antibacterials, and as a result the degerming final formulations represent some degree of compromise. Mildness is often obtained at the expense of effective degerming or effective cleansing and lathering which may be sacrificed for either mildness, product stability, or both.

The present invention offers a valuable combination of desirable properties to liquid skin-cleaning formulations.

Therefore, one object of this invention is the development of liquid skin cleaning compositions which exhibit improved mildness with good cleaning and lathering, and good degerming properties.

Other objects will become apparent from the detailed description below.

SUMMARY OF THE INVENTION

A stable liquid emulsion personal cleansing composition comprising:
(a) from about 0.1 parts to about 20 parts by weight of anionic surfactant,
(b) from about 0.1 parts to about 20 parts by weight of amphoteric surfactant,
(c) from about 0.5 parts to about 25 parts by weight of an oily skin moisturizer, preferably an adduct prepared from vegetable oils containing non-conjugated polyunsaturated fatty acid esters which are conjugated and elaidinized and then modified via Diels-Alder addition with a member of the group consisting of acrylic acid, fumaric acid and maleic anhydride,
(d) from about 0.1 parts to about 2.0 parts antibacterial agent; and
(e) water,
wherein the anionic surfactant and amphoteric surfactant together comprise from about 0.5 parts to about 30 parts by weight of the composition, and where the weight ratio of anionic surfactant:amphoteric surfactant is in the range from about 1:5 to about 20:1.

DETAILED DESCRIPTION OF THE INVENTION

The liquid cleansers of this invention are first highly preferred, especially for use as a body wash, because of its convenience and non-messiness. Secondly, they are antibacterial personal cleansers so they kill germs. Thirdly, they are very mild personal cleansers so they minimize skin irritation, dryness, etc. The personal cleansing compositions of this invention have all three of these preferred characteristics which are very desirable for liquid cleanser body wash users.

A stable liquid emulsion personal cleansing composition comprising:
(a) from about 0.1 parts to about 20 parts, preferably 1 part to 15 parts, especially 3 to 12 parts by weight of anionic surfactant,
(b) from about 0.1 parts to about 20 parts, preferably 1 part to 15 parts, especially 3 to 12 parts by weight of amphoteric surfactant.
(c) from about 0.5 parts to about 25 parts, preferably 0.5 parts to 15 parts, especially 3 parts to about 10 parts by weight of an oily skin moisturizer, preferably an adduct prepared from vegetable oils containing non-conjugated polyunsaturated fatty acid esters which are conjugated and elaidinized and then modified via Diels-Alder addition with a member of the group consisting of acrylic acid, fumaric acid and maleic anhydride.

(d) from about 0.1 parts to about 2.0 parts antibacterial agent; and (e) water, wherein the anionic surfactant and amphoteric surfactant together comprise from about 0.5 parts to about 30 parts, preferably 5 parts to 25 parts, especially 10 parts to 20 parts by weight of the composition, and where the weight ratio of anionic surfactant:amphoteric surfactant is in the range from about 1:5 to about 20:1, preferably 1:2 to about 5:1, especially 1:1 to about 2:1.

The anionic surfactant is selected from the group consisting of ethoxylated alkyl sulfates, alkyl glyceryl ether sulfonates, methyl acyl taurates, fatty acyl glycinates, N-acyl glutamates, acyl isethionates, alkyl sulfosuccinates, alphasulfonated fatty acids, their salts and/or their esters, alkyl phosphate esters, ethoylated alkyl phosphate esters, acyl sarcosinates and fatty acid/protein condensates, and mixtures thereof.

The amphoteric surfactant is selected from the group consisting of:

(a) imidazolinium derivatives of formula (II)

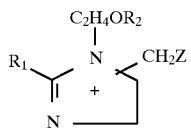

wherein $R_1$ is $C_7$–$C_{22}$ alkyl or alkenyl, $R_2$ is hydrogen or $CH_2Z$, each Z is independently $CO_2M$ or $CH_2CO_2M$, and M is H, alkali metal, alkaline earth metal, ammonium or alkanolammonium; and/or ammonium derivatives of formula (III)

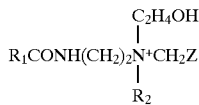

wherein $R_1$, $R_2$ and Z are as defined above:

(b) aminoalkanoates of formula (IV)

and iminodialkanoates of formula (V)

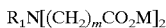

wherein n and m are numbers from 1 to 4, and $R_1$ and M are independently selected from the groups specified in (a) above; and (c) mixtures thereof The composition has a viscosity (Brookfield RVT, Spindle 5, 50 rpm, 25° C.) is preferably at least about 1,000 cps, more preferably about 2,000 to 10,000 cps, especially from about 5,000 to about 7,000 cps, and has an average emulsion droplet size of about 0.1 to about 40 microns.

The preferred compositions have non-Newtonian viscosity characteristics; for example, the preferred compositions have a viscosity (Brookfield RVT, Helipath, Spindle T-B, 5 rpm, 25° C., 1 min) in the range of from about 10,000 to about 40,000 cps, more preferably from about 20,000 to about 30,000 cps.

The essential as well as a variety of optional components of the compositions of the present invention are described below.

Alkyl Ethoxylated Sulfate

The mild personal liquid cleanser composition hereof comprises from about 0.1 parts to about 20 parts, preferably 1 part to 15 parts, especially 3 parts 12 parts by weight of an alkyl ethoxylated sulfate anionic surfactant.

Alkyl ethoxylated sulfate surfactants are well known in the art, and can be represented by the formula $RO(C_2H_4O)_xSO_3M$, wherein R is alkyl or alkenyl of from about 8 to about 24 carbon atoms, x is 1 to 12, preferably 2 to 6, and M is a water-soluble cation such as an alkali or alkaline earth metal, preferably, sodium, magnesium or potassium. The average degree of ethoxylated, i.e. the average value for x should be at least about 2.0.

Exemplary alkyl ethoxylated sulfates are condensation products of ethylene oxide and monohydric alcohols having from about 8 to about 24 carbon atoms. Preferably, R has from about 10 to about 18 carbon atoms. The alcohols can be derived from fats, e.g., coconut oil or tallow, or can be synthetic. Lauryl alcohol and straight chain alcohols derived from coconut oil are preferred herein. Such alcohols are typically reacted with from about 2 to about 12, preferably about 2 to about 6, more preferably about 3, molar proportions of ethylene oxide and the resulting mixture of molecular species having, for example, an average moles of ethylene oxide per mole of alcohol also within the above limits, is sulfated and neutralized.

Specific examples of alkyl ethoxylated sulfates which may be used in the present invention are the salts, especially sodium, magnesium or potassium salts, of coconut alkyl triethylene glycol ethoxylated sulfate, tallow alkyl triethylene glycol ethoxylated sulfate, and tallow alkyl hexaoxyethylene sulfate. Typically the alkyl ether sulfates will comprise a mixture of individual compounds, said mixture preferably having an average alkyl chain length of from about 10 to about 16 carbon atoms, and an average degree of ethoxylation of from about 2 to about 6 moles of ethylene oxide. Especially preferred are narrow range alkyl ethoxylated sulfates such as those having ethoxylation levels primarily in the range of about 2 to about 6.

Amphoteric Surfactant

The amphoteric surfactant will be present in the mild personal liquid cleanser compositions hereof at levels of from about 0.1 parts to about 20 parts, preferably 1 part to 15 parts, especially 3 to 12 parts by weight of anionic surfactant. The amphoteric component hereof is selected from the group consisting of amphoteric betaine, imidazoline, aminoalkanoate, and iminodialkanoate surfactants. Preferably, the ratio of the alkyl ethoxylated surfactant to the amphoteric surfactant will be from about 1:5 to about 20:1, more preferably 1:2 to about 5:1, especially 1:1 to about 2:1.

The imidazoline amphoteric surfactants hereof are depicted by Formula I:

wherein $R_1$ is $C_8$–$C_{22}$ alkyl or alkenyl, preferably $C_{12}$–$C_{16}$, $R_2$ is hydrogen or $CH_2CO_2M$, $R_3$ is $CH_2CH_2OH$ or $CH_2CH_2OCH_2CH_2COOM$, $R_4$ is hydrogen, $CH_2CH_2OH$, or $CH_2CH_2OCH_2CH_2COOM$, Z is $CO_2M$ or $CH_2CO_2M$, n is 2 or 3, preferably 2, M is hydrogen or a cation, such as alkali metal or alkaline earth metal. Examples of "alkali metal" include lithium, sodium, and potassium. Examples of "alkaline earth metal" include beryllium, magnesium, calcium, strontium, and barium. This type of surfactant is classified herein as an "imidazoline" amphoteric surfactant for convenience, although it should be recognized that it does not necessarily have to be derived, directly or indirectly, through an imidazoline intermediate.

Suitable materials of this type are marketed under the tradename MIRANOL and are understood to comprise a complex mixture of species, and can exist in protonated and non-protonated species depending upon pH with respect to species that can have a hydrogen at $R_2$. All such variations and species are meant to be encompassed herein.

Preferred surfactants of Formula I are monocarboxylates and dicarboxylates. Examples of these materials include cocoamphocarboxypropionate, cocoamphocarboxypropionic acid, cocoamphocarboxyglycinate (alternately referred to as cocoamphodiacetate), and cocoamphoacetate (alternately, cocoamphomonoacetate).

Specific commercial products providing the amphoteric surfactant component of the present compositions include those sold under the trade names MIRANOL C2M CONC. N.P., MIRANOL C2M CONC. O.P., MIRANOL C2M SF, MIRANOL CM SPECIAL (Miranol, Inc.); ALKATERIC 2CIB (Alkaril Chemicals); AMPHOTERGE W-2 (Lonza, Inc.); MONATERIC CDX-38, MONATERIC CSH-32 (Mona Industries); REWOTERIC AM-2C (Rewo Chemical Group); and SCHERCOTERIC MS-2 (Scher Chemicals).

Suitable betaine surfactants hereof are depicted by compounds having the Formula (II):

$$R_5 \left[ \begin{array}{c} O \quad R_4 \\ \| \quad | \\ -C-N-(CH_2)_m \end{array} \right]_n \left[ \begin{array}{c} R_2 \\ | \\ -N^+-Y-R_1 \\ | \\ R_3 \end{array} \right] \quad (II)$$

wherein:

$R_1$ is a member selected from the group consisting of $$COOM \text{ and } CH-CH_2SO_3M$$
$$\quad\quad\quad\quad\quad\quad | $$
$$\quad\quad\quad\quad\quad\quad OH$$

$R_2$ is lower alkyl or hydroxyalkyl;

$R_3$ is lower alkyl or hydroxyalkyl;

$R_4$ is a member selected from the group consisting of hydrogen and lower alkyl;

$R_5$ is higher alkyl or alkenyl;

Y is lower alkyl, preferably methyl;

m is an integer from 2 to 7, preferably from 2 to 3;

n is the integer 1 or 0;

M is hydrogen or a cation, such as an alkali metal or alkaline earth metal.

The term "lower alkyl" or "hydroxyalkyl" means straight or branch chained, saturated, aliphatic hydrocarbon radicals and substituted hydrocarbon radicals having from one to about three carbon atoms such as, for example, methyl, ethyl, propyl, isopropyl, hydroxypropyl, hydroxyethyl, and the like. The term "higher alkyl or alkenyl" means straight or branch chained saturated (i.e., "higher alkyl") and unsaturated (i.e., "higher alkenyl") aliphatic hydrocarbon radicals having from about eight to about 20 carbon atoms such as, for example, lauryl, cetyl, stearyl, oleyl, and the like.

Examples of surfactant betaines of Formula II wherein n is zero which are useful herein include the alkylbetaines such as cocodimethylcarboxymethylbetaine, lauryldimethylcarboxymethylbetaine, lauryl dimethyl-alpha-carboxyethylbetaine, cetyldimethylcarboxymethylbetaine, lauryl-bis-(2-hydroxyethyl)carboxymethylbetaine, stearyl-bis-(2-hydroxypropyl)carboxymethylbetaine, oleyldimethyl-gamma-carboxypropylbetaine, lauryl-bis-(2-hydroxypropyl)alpha-carboxyethylbetaine, etc. The sulfobetaines may be represented by cocodimethylsulfopropylbetaine, stearyldimethylsulfopropylbetaine, lauryl-bis-(2-hydroxyethyl)sulfopropylbetaine, and the like.

Amido betaines and amidosulfo betaine surfactants useful in the present invention are exemplified by compounds of Formula II wherein n is one but otherwise corresponding to the above examples. Examples of surfactant betaines of Formula II wherein n is one which are useful herein include the amidocarboxybetaines, such as cocoamidodimethylcarboxymethylbetaine, laurylamidodimethylcarboxymethylbetaine, cetylamidodimethylcarboxymethylbetaine, laurylamido-bis-(2-hydroxyethyl)-carboxymethylbetaine, cocoamido-bis-(2-hydroxyethyl)-carboxymethylbetaine, etc. The amido sulfobetaines may be represented by cocoamidodimethylsulfopropylbetaine, stearylamidodimethylsulfopropylbetaine, laurylamido-bis-(2-hydroxyethyl)-sulfopropylbetaine, and the like.

The preferred betaine in the present invention is a member selected from the group consisting of surfactant amidocarboxybetaines and amidosulfobetaines. More preferred betaines are the surfactant amidocarboxybetaines, particularly cocoamidodimethylcarboxymethylbetaines (cocomidopropylbetaine), such as those sold by Goldschmidt Co. under the trade name Tegobetaine (F grade), and by Hoechst-Celanese under the trade name Genagen CAB. These most preferred betaines have the formula:

$$R'_3-C-NH-(CH_2)_3-N-CH_2-COOM$$
with $O$ double-bonded to C and two $CH_3$ groups on N wherein $R'_3$ is selected from C8 to C18 alkyl radicals and M is hydrogen or a cation as defined above. In general, the preferred betaines hereof will have low levels of residual amide and sodium monochloroacetate.

Suitable aminoalkanoates and iminodialkanoates are represented by the Formulas (III) and (IV):

aminoalkanoates of the formula:

$$R-NH(CH_2)_nCOOM \quad\quad\quad (III);$$

and iminodialkanoates of the formula:

$$R-N[(CH_2)_mCOOM]_2 \quad\quad\quad (IV)$$

wherein n and m are from 1 to 4, R is $C_8-C_{22}$ alkyl or alkenyl, and M is hydrogen or alkali or an alkaline earth metal as previously described.

Examples of amphoteric surfactants falling within the aminoalkanoate formula include n-alkylamino-propionates and n-alkyliminodipropionates. Such material are sold under the tradename DERIPHAT by Henkel and MIRATANE by Miranol, Inc. Specific examples include N-lauryl-betaamino propionic acid or salts thereof, and N-lauryl-beta-imino-dipropionic acid (DERIPHAT 160C) or salts thereof, and mixtures thereof.

Oily Skin Moisturizers

The oily skin moisturizers will be present in the mild personal liquid cleanser compositions hereof at levels of from about 0.5 parts to about 25 parts by weight. The term "oily skin moisturizer" as used herein means any suitable lipid that can be used to moisturize the skin. The oily skin moisturizer should preferably be an adduct prepared from vegetable oils containing non-conjugated polyunsaturated fatty acid esters which are conjugated and elaidinized and then modified via Diels-Alder addition with a member of the group consisting of acrylic acid, fumaric acid and maleic anhydride. The adducts and their preparation are described in U.S. Pat. No. 4,740,367, Force, et al., Apr. 26, 1988, incorporated herein by reference, the adducts being marketed under the trade name Ceraphyl GA (Van Dyke). Preferred vegetable oil adducts are those prepared from soybean oil and adducts derived by Dies-Alder addition of vegetable oils with fumaric acid. A preferred method of preparing adducts herein is to react two moles of vegetable oil with one mole of the dienophile in the presence of catalytic amounts of iodine, the conjugation and elaidinization agent. This produces a 50:50 blend of adduct together with the disproportionated (conjugated) vegetable oil.

Antibacterial agent

The antibacterial agent will be present in the mild personal liquid cleanser compositions hereof at levels of from about 0.1 parts to about 1.0 part. The level is selected to provide the desired level of antibacterial activity and can be modified as desired. The preferred antibacterial agent is 2-hydroxy-4,2',4'-trichlorodiphenylether (TCS). Other halogenated antibacterial agents are set out below. Mixtures of these agents can also be used. Many antibacterial agents, known to those skilled in the art and disclosed in, e.g., U.S. Pat. Nos. 3,835,057 and 4,714,563, both incorporated herein before by reference, may be used.

Suitable antibacterial agents include:

2-hydroxy-4,2',4'-trichlorodiphenylether (TCS);

2,6-dimethyl-4-hydroxychlorobenzene (PCMX);

3,4,4'-trichlorocarbanilide (TCC);

3-trifluoromethyl-4,4'-dichlorocarbanilide (TFC);

2,2'-dihydroxy-3,3',5,5',6,6'-hexachlorodiphenylmethane;

2,2'-dihydroxy-3,3',5,5'-tetrachlorodiphenylmethane;

2,2'-dihydroxy-3,3',dibromo-5,5'-dichlorodiphenylmethane;

2-hydroxy4,4'-dichlorodiphenylether;

2-hydroxy-3,5',4-tribromodiphenylether; and 1-hydroxyl-4-methyl-6-(2,4,4-trimethylpentyl)-2(1H)-pyridinone (Octopirox).

The composition of this invention is preferably free of Oxeco, phenoxyisopropanol.

Water

The mild personal liquid cleanser composition hereof will also comprise water from about 40 parts by weight to about 80 parts by weight.

Mild personal liquid cleanser Compositions

The mild personal liquid cleanser hereof is substantially free of alkyl sulfate surfactants since alkyl sulfates are relatively harsh to the skin. It is recognized that there will generally be some alkyl sulfate present as a result of it being present in commercially available alkyl ethoxylated sulfate raw materials. For example, commercially available alkyl (3)ethoxylated sulfate typically contains about 20 parts by weight alkyl sulfate; commercially available alkyl(2) ethoxylated sulfate, about 25 parts to about 40 parts alkyl sulfate. For purposes hereof, substantially free of alkyl sulfate means the compositions hereof should have an alkyl sulfate:alkyl ethoxylated sulfate (average degree of ethoxylation of 2.5 and above) weight ratio of no more than about 0.35, preferably no more than about 0.30, more preferably no more than about 0.25. For alkyl ethoxylated sulfate with an average ethoxylation level of less than 2.5, the ratio should be no more than about 0.40, preferably no more than about 0.35, more preferably no more than about 0.30, most preferably no more than about 0.25. It is preferred that no additional amount of alkyl sulfate be added other than that which occurs inherently with the alkyl ethoxylated sulfate.

Narrow range ethoxylates can be used to lower the alkyl sulfate:alkyl ethoxylated sulfate weight ratio. "Narrow range ethoxylates" refer to alkyl ethoxylated sulfate surfactants that have been processed to reduce alkyl sulfates and, optionally, alkyl ethoxylated sulfates outside of the desired range of ethoxylation. The use of narrow range ethoxylates can be used to lower the alkyl sulfate:alkyl ethoxylated sulfate weight ratio, including to ratios as low as about 0.2 or even about 0.1, and less.

It is also preferred that no other ingredients that are unduly harsh to the skin be added to the mild personal liquid cleanser compositions hereof.

Additional Ingredients

The compositions of the present invention can contain a wide variety of optional ingredients useful or known for use in the art for hand soaps and other mild personal liquid cleanser compositions. Exemplary additional ingredients are described below.

Additional surfactants that can be used include other anionic, nonionic, and amphoteric surfactants, as well as zwitterionic and cationic surfactants.

Anionic Surfactants

A suitable class of anionic surfactants are the water-soluble, organic salts of the general formula:

$$R_1\text{—}SO_3\text{—}M$$

wherein $R_1$ is chosen from the group consisting of a straight or branched chain, saturated aliphatic hydrocarbon radical having from about 8 to about 24, preferably about 12 to about 18, carbon atoms; and M is a cation. Important examples are the salts of an organic sulfuric acid reaction product of a hydrocarbon of the methane series, including iso-, neo-, and n-paraffins, having about 8 to about 24 carbon atoms, preferably about 12 to about 18 carbon atoms and a sulfonating agent, e.g., $SO_3$, $H_2SO_4$, oleum, obtained according to known sulfonation methods, including bleaching and hydrolysis. Preferred are alkali metal sulfonated $C_{12-18}$ paraffins.

Additional examples of anionic surfactants which come within the terms of the present invention are the reaction products of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil. Other anionic synthetic surfactants of this variety are set forth in U.S. Pat. Nos. 2,486,921; 2,486,922; and 2,396,278; incorporated by reference.

Still other anionic surfactants include the class designated as succinamates. This class includes such surface active agents as disodium N-octadecylsulfosuccinamate; tetrasodium N-(1,2-dicarboxyethyl)-N-octadecylsulfosuccinamate; diamyl ester of sodium sulfosuccinic acid; dihexyl ester of sodium sulfosuccinic acid; dioctyl esters of sodium sulfosuccinic acid.

Other suitable anionic surfactants utilizable herein are olefin sulfonates having about 12 to about 24 carbon atoms. The term "olefin sulfonates" is used herein to mean compounds which can be produced by the sulfonation of a-olefins by means of uncomplexed sulfur trioxide, followed by neutralization of the acid reaction mixture in conditions such that any sulfones which have been formed in the reaction are hydrolyzed to give the corresponding hydroxyalkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form.

Another class of anionic surfactants are the b-alkyloxy alkane sulfonates. These compounds have the following formula:

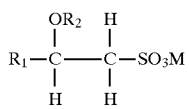

where $R_1$ is a straight chain alkyl group having from about 6 to about 20 carbon atoms, $R_2$ is a lower alkyl group having from about 1 (preferred) to about 3 carbon atoms, and M is a water-soluble cation.

Many additional synthetic anionic surfactants are described in *McCutcheon's Emulsifiers and Detergents,* 1989 *Annual,* published by M. C. Publishing Co., which is incorporated herein by reference. Also U.S. Pat. No. 3,929,678, Laughlin et al., issued Dec. 30, 1975, discloses many other anionic as well as other surfactant types and is incorporated herein by reference. Soaps, of course, also fall within the scope of anionic detersive surfactants that can be used.

Nonionic Surfactants

A wide variety of nonionic surfactants can be used. Nonionic surfactants include those broadly defined as compounds produced by the condensation of alkylene oxide groups (hydrophilic in nature) with an organic hydrophobic compound, which may be aliphatic or alkyl aromatic in nature. Examples of classes of nonionic surfactants are:

1. The polyethylene oxide condensates of alkyl phenols, e.g., the condensation products of alkyl phenols having an alkyl group containing from about 6 to about 20 carbon atoms, preferably from about 6 to about 12, in either a straight chain or branched chain configuration, with ethylene oxide, the said ethylene oxide being present in amounts equal to from about 10 to about 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40 parts to about 80 parts polyoxyethylene by weight and having a molecular weight of from about 5,000 to about 11,000 resulting from the reaction of ethylene oxide groups with a hydrophobic base constituted of the reaction product of ethylene diaamine and excess propylene oxide, said base having a molecular weight of the order of about 2,500 to about 3,000, are satisfactory.

3. The condensation product of aliphatic alcohols having from about 8 to about 18 carbon atoms, in either straight chain or branched chain configuration, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms.

4. Long chain tertiary amine oxides corresponding to the following general formula:

$$R_1R_2R_3N \rightarrow O$$

wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyldodecylamine oxide, oleyldi(2-hydroxyethyl)amine oxide, dimethyloctylamine oxide, dimethyl-decylamine oxide, dimethyl-tetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl) amine oxide, dimethylhexadecylamine oxide.

5. Long chain tertiary phosphine oxides corresponding to the following general formula:

$$RR'R''P \rightarrow O$$

wherein R contains an alkyl, alkenyl or monohydroxyalkyl radical ranging from about 8 to about 18 carbon atoms in chain length, from 0 to about 10 ethylene oxide moieties and from 0 to about 1 glyceryl moiety and R' and R" are each alkyl or monohydroxyalkyl groups containing from about 1 to about 3 carbon atoms. The arrow in the formula is a conventional representation of a semipolar bond. Examples of suitable phosphine oxides are: dodecyldimethylphosphine oxide, tetradecyldimethylphosphine oxide, tetradecylmethylethylphosphine oxide, 3,6,9,-trioxaoctadecyldimethylphosphine oxide, cetyldimethylphosphine oxide, 3-dodecoxy-2-hydroxypropyldi(2-hydroxyethyl)phosphine oxide, stearyldimethylphosphine oxide, cetylethylpropylphosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dodecyldi(2-hydroxyethyl)phosphine oxide, tetradecylmethyl-2-hydroxypropylphosphine oxide, oleydimethylphosphine oxide, 2-hydroxydodecyldimethylphosphine oxide.

6. Long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glyceryl moiety. Examples include: octadecyl methyl sulfoxide, 2-ketotridecyl methyl sulfoxide, 3,6,9,-trixaoctadecyl 2-hydroxyethyl sulfoxide, dodecyl methyl sulfoxide, oleyl 3-hydroxypropyl sulfoxide, tetradecyl methyl sulfoxide, 3-methoxytridecyl methyl sulfoxide, 3-hydroxytridecyl methyl sulfoxide, 3-hydroxy-4-dodecoxybutyl methyl sulfoxide.

7. Polysorbates, e.g., sucrose esters of fatty acids. Such materials are described in U.S. Pat. No. 3,480,616, e.g., sucrose cocoate (a mixture of sucrose esters of a coconut acid, consisting primarily of monoesters, and sold under the tradenames GRILLOTEN LSE 87K from RITA, and CRODESTA SL-40 from Croda).

8. Alkyl polysaccharide nonionic surfactants are disclosed in U.S. Pat. No. 4,565,647, Llenado, issued Jan. 21, 1986, having a hydrophobic group containing from about 6 to about 30 carbon atoms, preferably from about 10 to about 16 carbon atoms and a polysaccharide, e.g., a polyglycoside, hydrophilic group. The polysaccharide can contain from about 1.0 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties. (Optionally the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6-positions on the preceding saccharide units.

Optionally, and less desirably, there can be a polyalkyleneoxide chain joining the hydrophobic moiety and the polysaccharide moiety. The preferred alkyleneoxide is ethylene oxide. Typical hydrophobic groups include alkyl groups, either saturated or unsaturated, branched or unbranched containing from about 8 to about 18, preferably from about 10 to about 16, carbon atoms. Preferably, the alkyl group is a straight chain saturated alkyl group. The alkyl group can contain up to about 3 hydroxy groups and/or the polyalkyleneoxide chain can contain up to about 10, preferably less than 5, alkylene moieties. Suitable alkyl polysaccharides are octyl, nonyldecyl, undecyldodecyl, tridecyl, tetradecyl, pentadecyl, hexadecyl, heptadecyl, and octadecyl, di-, tri-, tetra-, penta-, and hexaglucosides, galactosides, lactosides, glucoses, fructosides, fructoses and/or galactoses. Suitable mixtures include coconut alkyl, di-, tri-, tetra-, and pentagluscosides and tallow alkyl, tetra-, penta-, and hexaglucosides.

9. Polyethylene glycol (PEG) glyceryl fatty esters, as depicted by the formula $RC(O)OCH_2CH(OH)CH_2(OCH_2CH_2)_nOH$ wherein n is from about 5 to about 200, preferably from about 20 to about 100, more preferably from about 30 to about 85, and RC(O)— is an ester wherein R comprises an aliphatic radical having from about 7 to 19 carbon atoms, preferably from about 9 to 17 carbon atoms, more preferably from about 11 to 17 carbon atoms, most preferably from about 11 to 14 carbon atoms. The combinations of n from about 20 to about 100, with $C_{12}$–$C_{18}$, preferably $C_{12}$–$C_{15}$ fatty esters, for minimized adverse effect on foaming, is preferred.

Suitable glyceryl fatty ester portions of these surfactants include glyceryl cocoate, glyceryl tallowate, glyceryl palmate, glyceryl stearate, glyceryl laurate, glyceryl oleate, glyceryl ricinoleate, and glyceryl fatty esters derived from triglycerides, such as palm oil, almond oil, and corn oil.

Other surfactants that can be used include soluble cationic surfactants, such as quaternary ammonium surfactants, and other amphoteric and zwitterionic surfactants known to those in the art.

Cationic cellulose ether derivatives

The mild personal liquid cleanser compositions of the present invention may comprise of a cationic cellulose ether derivative.

Cationic cellulose ether derivatives, for purposes hereof, is a polymeric quaternary ammonium salt of hydroxyethyl cellulose reacted with a trimethyl ammonium substituted epoxide.

Foam enhancers are well known in the art. Polyquaternium-10 (an industry term designated by the Cosmetic, Toiletry and Fragrance Association (CFTA) for a polymeric quaternary ammonium salt of hydroxyethyl cellulose reacted with a trimethyl ammonium substituted epoxide is a preferred polymer for foam enhancement. Polyquaternium-10 is commercially available from Union Carbide Corp. (Danbury, Conn. U.S.A.) under their UCARE POLYMER JR series of materials, e.g., UCARE POLYMER JR-30M, JR-125, and JR400.

Conditioning Agents

Another component includes the addition of petrolatum. Petrolatum can be any grade of white or yellow petrolatum recognized in the art as suitable for human application. The preferred type is USP Class III with a melting point between 122° and 135° F. (50° and 57° C.). Such a material is commercially available as Penreco Snow White Pet USP. The petrolatum in this invention includes hydrocarbon mixtures formulated with mineral oils in combination with paraffin waxes of various melting points. Preferred conditioning agents of this type are disclosed in U.S. patent application Ser. No. 07/909,834, Dias, et al., filed Jul. 7, 1992, and U.S. patent application Ser. No. 07/909,877, Kacher, et al., filed Jul. 7, 1992, allowed and incorporated herein by reference.

Examples of other moisturizers include the water soluble hexadecyl, myristyl, isodecyl or isopropyl esters of adipic, lactic, oleic, stearic, myristic or linoleic acids, as well as many of their corresponding alcohol esters (sodium isostearoyl-2-lactylate, sodium capryl lactylate), polyethyleneglycol esters such as PEG(6)caprylic/capryl glycerate (Softigan 767), hydrolyzed protein and other collagen-derived proteins, aloe vera gel and acetamide MEA.

An optional component hereof is a soluble conditioning agent suitable for conditioning hair or skin. Skin conditioning proteolytic enzyme can also be used.

Suitable conditioners include, for example, soluble polyether siloxane copolymer, such as a polypropylene oxide modified dimethylpolysiloxane (e.g., Dow Corning DC-1248), although ethylene oxide or mixtures of ethylene oxide and propylene oxide may also be used. The ethylene oxide and polypropylene oxide level must be sufficiently high to provide solubility in water and the composition hereof.

Other Optional Components

The skin cleansers herein can contain a variety of nonessential, optional ingredients suitable for improving such compositions in a variety of ways. Such conventional, optional ingredients are well known to those skilled in the art, e.g., preservatives such as HMDM Hydantoin, benzyl alcohol, methyl paraben, propyl paraben, 3-isothiazolines (Kathon CG sold by Rohm and Haas), imidazolidinyl urea, methylchloroisothiazolinone, and methylisothiazolinone can be used in amounts of from 1 to 5,000 ppm; thickeners and viscosity modifiers such as sodium sulfate, polyethylene glycols, sodium chloride, ammonium chloride, carboxymethylcellulose, methylcellulose, polyvinyl alcohol, and ethyl alcohol; suspending agents such as magnesium/aluminum silicate; perfumes, dyes; opacifiers such as ethylene glycol distearate, glycol monostearate, styrene acrylate copolymer, mica, behenic acid, and calcium stearate; sequestering agents such as disodium ethlyenediamine tetraacetate; emollients, moisturizers and various other skin treating ingredients such as glycerin; buffers and builders such as citrates and phosphates. If present, such agents individually generally comprise from about 0.01 parts to about 5 parts by weight of the composition.

Implement

A body puff or sponge which is made of nylon mesh in the shape of a round sponge (about 4.5 inches in diameter)

which when used in conjunction with this invention, is an effective system which enhances the delivery of mild skin cleansing and skin conditioning benefits. Such a puff is manufactured by the sponge factory (Bilange). The puff is comprised of three pieces of extruded tubular netting (scrim) which is folded numerous times to form a soft ball-like sponge, with a nylon rope attached.

METHOD OF USE

In its method aspect, the present invention comprises a method of washing the skin by contacting the skin with an amount of the cleanser compositions herein which is effective to clean the skin and rinsing the excess cleanser from the skin. An effective amount for any individual will depend upon variable factors such as amount of soil on the skin, type of soil on the skin, level of surfactant in the cleanser composition, etc. Generally, an effective amount will be from about 0.5 to about 5 grams per use.

EXAMPLES

The invention is illustrated by the following non-limiting examples.

In the examples, all concentration are on a 100 parts active basis and the abbreviations have the following designation:

| | |
|---|---|
| Anionic | Sodium Magnesium Laureth 3.6 Sulfate |
| Amphoteric 1 | Sodium Lauroamphoacetate |
| Amphoteric 2 | Cocamidopropyl Betaine |
| Nonionic | Cocamide MEA |
| Oil 1 | Maleated Soybean Oil |
| Oil 2 | Soybean Oil |
| Polymer | Polyquaternium-10 |
| Antibact 1 | 2-hydroxy-4,2',4'-trichlorodiphenylether |
| Antibact 2 | 3,4,4'-trichlorocarbanilide |
| Preservative | DMDM Hydantoin |
| Thickener 1 | Palm Kernal Fatty Acid |
| Thickener 2 | Magnesium Sulfate |
| Glyceride | Peg-6 Caprylic/Capric Glycerides |

Examples I to VI

The following are personal cleansing compositions in the form of shower foam products and which are representative of the present invention:

| | I | II | III | IV | V | VI |
|---|---|---|---|---|---|---|
| Anionic | 10.0 | 12.0 | 12.0 | 12.0 | 10.0 | 12.0 |
| Amphoteric 1 | 5.0 | 6.0 | — | — | 5.0 | 6.0 |
| Amphoteric 2 | — | — | 6.0 | 6.0 | — | — |
| Nonionic | 2.8 | 2.8 | 2.8 | 2.8 | 2.8 | 2.8 |
| Oil 1 | 2.0 | 2.0 | 2.0 | 2.0 | 2.0 | 2.0 |
| Oil 2 | 8.0 | 8.0 | 8.0 | 8.0 | 8.0 | 8.0 |
| Glycerin | 3.0 | 3.0 | 3.0 | 3.0 | 3.0 | 3.0 |
| Polymer | 0.4 | 0.4 | 0.4 | 0.4 | 0.4 | 0.4 |
| Antibact 1 | 0.3 | 0.3 | 0.3 | — | — | — |
| Antibact 2 | — | — | — | 0.7 | 0.7 | 0.7 |
| Preservative | 0.2 | 0.2 | 0.2 | 0.2 | 0.2 | 0.2 |
| Thickener 1 | 1.9 | 1.9 | 1.9 | 1.9 | 1.9 | 1.9 |
| Thickener 2 | 0.1 | 0.1 | 0.1 | 0.1 | 0.1 | 0.1 |
| Glycerides | 4.0 | 4.0 | 4.0 | 4.0 | 4.0 | 4.0 |
| Fragrance | 1.0 | 1.0 | 1.0 | 1.0 | 1.0 | 1.0 |
| Water | | | to 100 | | | |

The above liquid cleansers are first highly preferred, especially for use as a body wash, because of convenience and non-messiness. Secondly, they are antibacterial personal cleansers that kill germs. Thirdly, they are very mild personal cleansers so they minimize skin irritation, dryness, etc. These personal cleansing compositions have all three of these preferred characteristics which are very desirable for liquid cleanser body wash users.

Example II is most preferred for its lather.

What is claimed is:

1. A liquid emulsion personal cleansing composition comprising, per 100 parts by weight of the composition:

(a) from about 0.1 parts to about 20 parts by weight of anionic surfactant comprising alkyl ethoxylated sulfate, (b) from about 0.1 parts to about 20 parts by weight of amphoteric surfactant comprising at least one of (i) imidazolinium derivatives of the formula

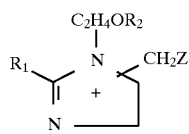

wherein $R_1$ is $C_7-C_{22}$ alkyl or alkenyl, $R_2$ is hydrogen or $CH_2Z$, each Z is independently $CO_2M$ or $CH_2CO_2M$, and M is H, alkali metal, alkaline earth metal, ammonium or alkanolammonium, or ammonium derivatives of the formula

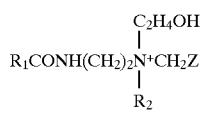

wherein $R_1$, $R_2$ and Z are as defined above; or (ii) aminoalkanoates of the formula $$R_1NH(CH_2)_nCO_2M$$

or iminodialkanoates of the formula $$R_1N((CH_2)_mCO_2M)_2$$

where n and m are numbers from 1 to 4, and $R_1$ and M are as defined above; and mixtures thereof, (c) from about 0.5 parts to about 25 parts by weight of an oil skin moisturizer comprising an adduct prepared from vegetable oils containing non-conjugated polyunsaturated fatty acid esters which are conjugated and elaidinized and then modified via Diels-Alder addition with a member of the group consisting of acrylic acid, fumaric acid and maleic anhydride, (d) from about 0.1 parts to about 2.0 parts by weight antibacterial agent, and (e) water, wherein the anionic surfactant and amphoteric surfactant together comprise from about 0.5 parts to about 30 parts by weight of the composition, wherein the weight ratio of anionic surfactant:amphoteric surfactant is in the range of from about 1:5 to about 20:1, wherein said composition has a viscosity (Brookfield RVT, Spindle 5, 50 rpm, 25° C.) of at least 1,000 cps and has an average emulsion droplet size of 0.1 to about 40 microns, and wherein the weight ratio of alkyl sulfate to alkyl ethoxylated sulfate is not greater than 0.2.

2. A liquid emulsion personal cleansing composition according to claim 1, comprising, per 100 parts by weight of the composition:

(a) from about 1 part to 15 parts by weight of the anionic surfactant, (b) from about 1 part to 15 parts by weight of the amphoteric surfactant, (c) from about 0.5 parts to 15 parts by weight of the oily skin moisturizer, (d) from about 0.1 parts to about 2.0 parts by weight of the antibacterial agent, and (e) water, wherein the anionic surfactant and amphoteric surfactant together comprise from about 5 parts to 25 parts by weight of the composition, wherein the weight ratio of anionic surfactant:amphoteric surfactant is in the range from about 1:2 to about 5:1, and wherein said composition has a viscosity (Brookfield RVT, Spindle 5, 50 rpm, 25° C.) of about 5,000 to 7,000 cps and has an average emulsion droplet size of about 0.1 to 40 microns.

3. A liquid emulsion personal cleansing composition according to claim 1, comprising, per 100 parts by weight of the composition:

(a) from about 3 to 12 parts by weight of the anionic surfactant, (b) from about 3 to 12 parts by weight of the amphoteric surfactant, (c) from about 3 parts to about 10 parts by weight of the oily skin moisturizer, (d) from about 0.1 parts to about 2.0 parts by weight of the antibacterial agent, and (e) water, wherein the anionic surfactant and amphoteric surfactant together comprise from about 10 parts to 20 parts by weight of the composition, wherein the weight ratio of anionic surfactant:amphoteric surfactant is in the range from about 1:1 to about 2:1, and wherein said composition has a viscosity (Brookfield RVT, Spindle 5, 50 rpm, 25° C.) of about 5,000 to 7,000 cps and has an average emulsion droplet size of about 0.1 to 40 microns.

4. A liquid emulsion personal cleansing compositions comprising, per 100 parts by weight of the composition:

(a) from about 0.1 parts to about 20 parts by weight of anionic surfactant, wherein the anionic surfactant comprises sodium magnesium laureth 3.6 sulfate;

(b) from about 0.1 parts to about 20 parts by weight of amphoteric surfactant, wherein the amphoteric surfactant comprises sodium lauroamphoacetate;

(c) from about 0.5 parts to about 25 parts by weight of an oily skin moisturizer which comprises moisturizers selected from the group consisting of maleated soybean oil, soybean oil, and mixtures thereof;

(d) from about 0.1 parts to about 2.0 parts by weight antibacterial agent, wherein the antibacterial agent comprises 2-hydroxy-4,2',4'-trichlorodiphenylether;

(e) a nonionic surfactant which comprises cocoamide MEA;

(f) a preservative;

(g) a thickener;

(h) a glyceride; and (i) water;

wherein the anionic surfactant and amphoteric surfactant together comprise from about 0.5 parts to about 30 parts by weight of the composition, wherein the weight ratio of anionic surfactant:amphoteric surfactant is in the range of from about 1:5 to about 20:1, wherein said composition has a viscosity of at least about 1,000 cps and an average emulsion droplet size ranging from 0.1 to about 40 microns, and wherein the weight ratio of alkyl sulfate to alkyl ethoxylated sulfate is not greater than 0.2.

5. A liquid emulsion personal cleansing composition comprising, per 100 parts by weight of the composition:

(a) from about 0.1 parts to about 20 parts by weight of anionic surfactant, wherein the anionic surfactant comprises sodium magnesium laureth 3.6 sulfate;

(b) from about 0.1 parts to about 20 parts by weight of amphoteric surfactant, wherein the amphoteric surfactant comprises sodium lauroamphoacetate;

(c) from about 0.5 parts to about 25 parts by weight of an oily skin moisturizer which comprises moisturizers selected from the group consisting of maleated soybean oil, soybean oil, and mixtures thereof;

(d) from about 0.1 parts to about 2.0 parts by weight antibacterial agent, wherein the antibacterial agent comprises 3,4,4'-trichlorocarbanilide;

(e) a nonionic surfactant which comprises cocoamide MEA;

(f) a preservative;

(g) a thickener;

(h) a glyceride; and (i) water;

wherein the anionic surfactant and amphoteric surfactant together comprise from about 0.5 parts to about 30 parts by weight of the composition, wherein the weight ratio of anionic surfactant:amphoteric surfactant is in the range of from about 1:5 to about 20:1, wherein said composition has a viscosity of at least about 1,000 cps and an average emulsion droplet size ranging from 0.1 to about 40 microns, and wherein the weight ratio of alkyl sulfate to alkyl ethoxylated sulfate is not greater than 0.2.

6. A liquid emulsion personal cleansing composition according to claim 1, wherein the amphoteric surfactant comprises sodium lauroamphoacetate or cocamidopropyl betaine.

7. A liquid emulsion personal cleansing composition according to claim 1, wherein the oily skin moisturizer comprises soybean oil, maleated soybean oil, or mixtures thereof.

8. A liquid emulsion personal cleansing composition according to claim 1, wherein the anionic surfactant comprises ethoxylated alkyl sulfate, the amphoteric surfactant comprises sodium lauroamphoacetate or cocamidopropyl betaine, and the oily skin moisturizer comprises soybean oil, maleated soybean oil or mixtures thereof.

* * * * *